United States Patent [19]

Chase et al.

[11] 4,346,742
[45] Aug. 31, 1982

[54] METHOD FOR DILUTING A LIQUID TEST SAMPLE AND COMPUTER CONTROLLD DILUTING APPARATUS

[75] Inventors: Charles Chase, Elk Groove; Stephen Walters, Citrus Heights; Richard E. Meador, Sacramento, all of Calif.

[73] Assignee: P.M. America, Inc., Sacramento, Calif.

[21] Appl. No.: 155,472

[22] Filed: Jun. 2, 1980

[51] Int. Cl.³ ................................................ B65B 3/32
[52] U.S. Cl. ..................................... 141/1; 73/864.12; 73/864.16; 141/27
[58] Field of Search .......... 73/864.12, 864.16, 864.18; 128/DIG. 1; 141/1 R, 2, 18, 21, 25, 27, 130, 1

[56] References Cited

U.S. PATENT DOCUMENTS

| | | | |
|---|---|---|---|
| 3,197,285 | 7/1965 | Rosen | 141/25 X |
| 3,901,084 | 8/1975 | Brailsford | 141/130 X |
| 3,915,651 | 10/1975 | Nishi | 73/864.16 |

*Primary Examiner*—Frederick R. Schmidt
*Attorney, Agent, or Firm*—Bruce & McCoy

[57] ABSTRACT

Improved method for the pick up and delivery of a liquid test sample and diluent therefore by a single syringe having a syringe valve for placing the syringe barrel in fluid connection with either a diluent pick up line or a sample pick-up line. The method is comprised essentially of the steps of priming the apparatus, picking up the diluent through the diluent pick-up line and thereafter with a continuing downward stroke of the syringe plunger picking up a percentage volume of liquid sample. Preferably, an air bubble is picked up in the end of the sample pick-up line before the sample pick-up cycle. After the full downward stroke of the syringe plunger, the diluted sample is delivered by depressing the plunger to its zero volume setting.

An apparatus is provided having a computer controlled syringe plunger drive which includes a zero volume switch, and a computer controlled syringe valve having branch ports adapted to be connected to a diluent and a sample pick-up line. The computer control sequences the plunger drive and the syringe valve to pick-up diluent and sample and deliver diluent and sample as above-described.

9 Claims, 7 Drawing Figures

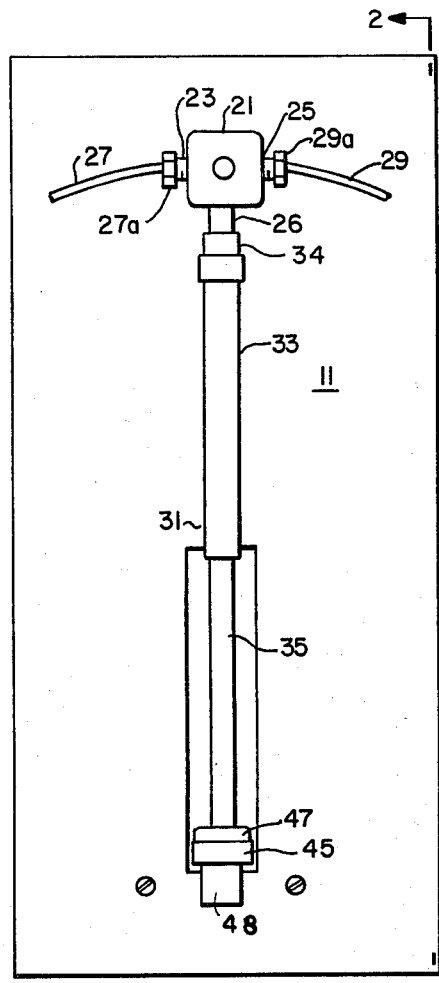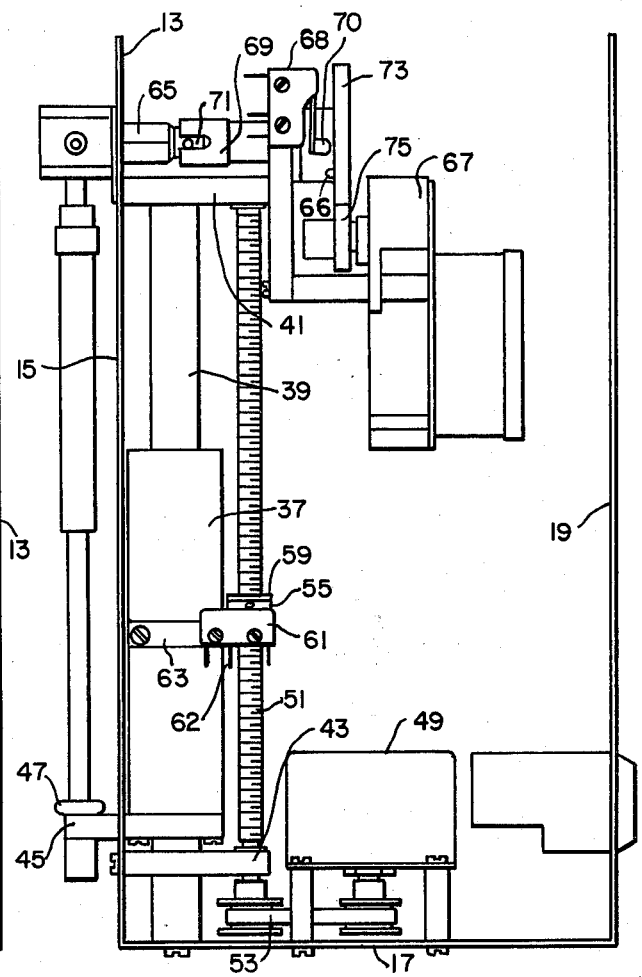
FIG.—1
FIG.—2
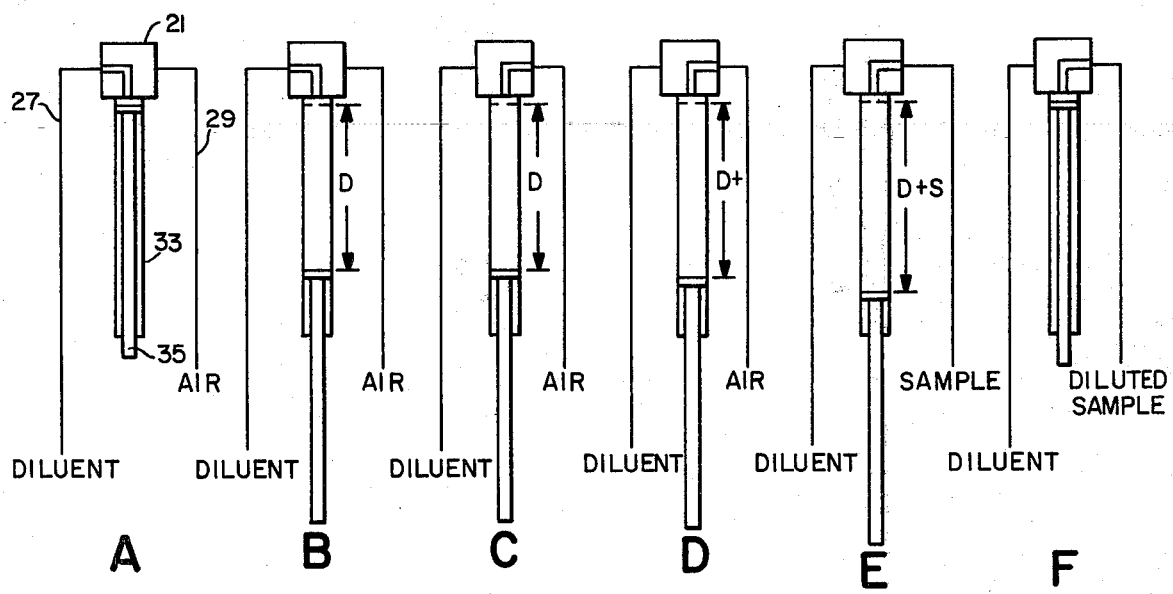
FIG.—3

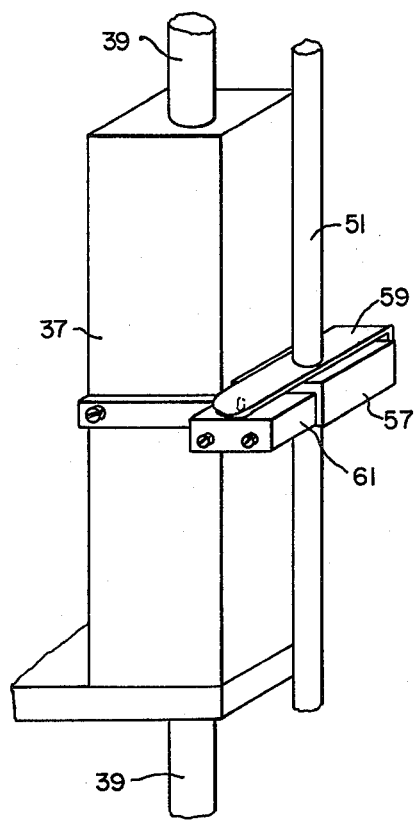
FIG.—4
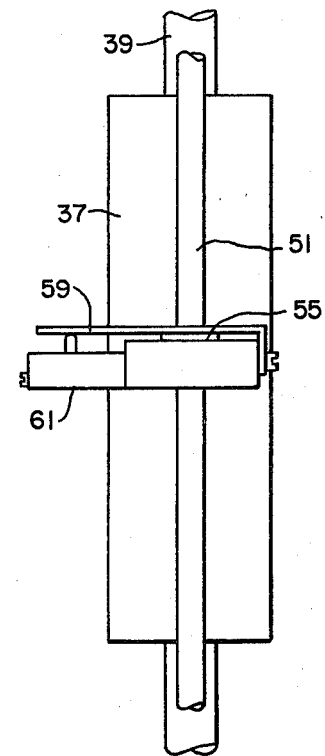
FIG.—5
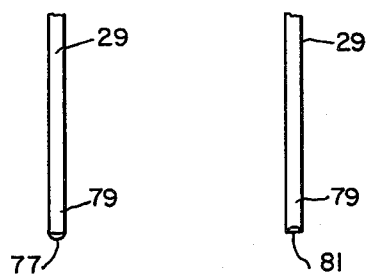
FIG.—6

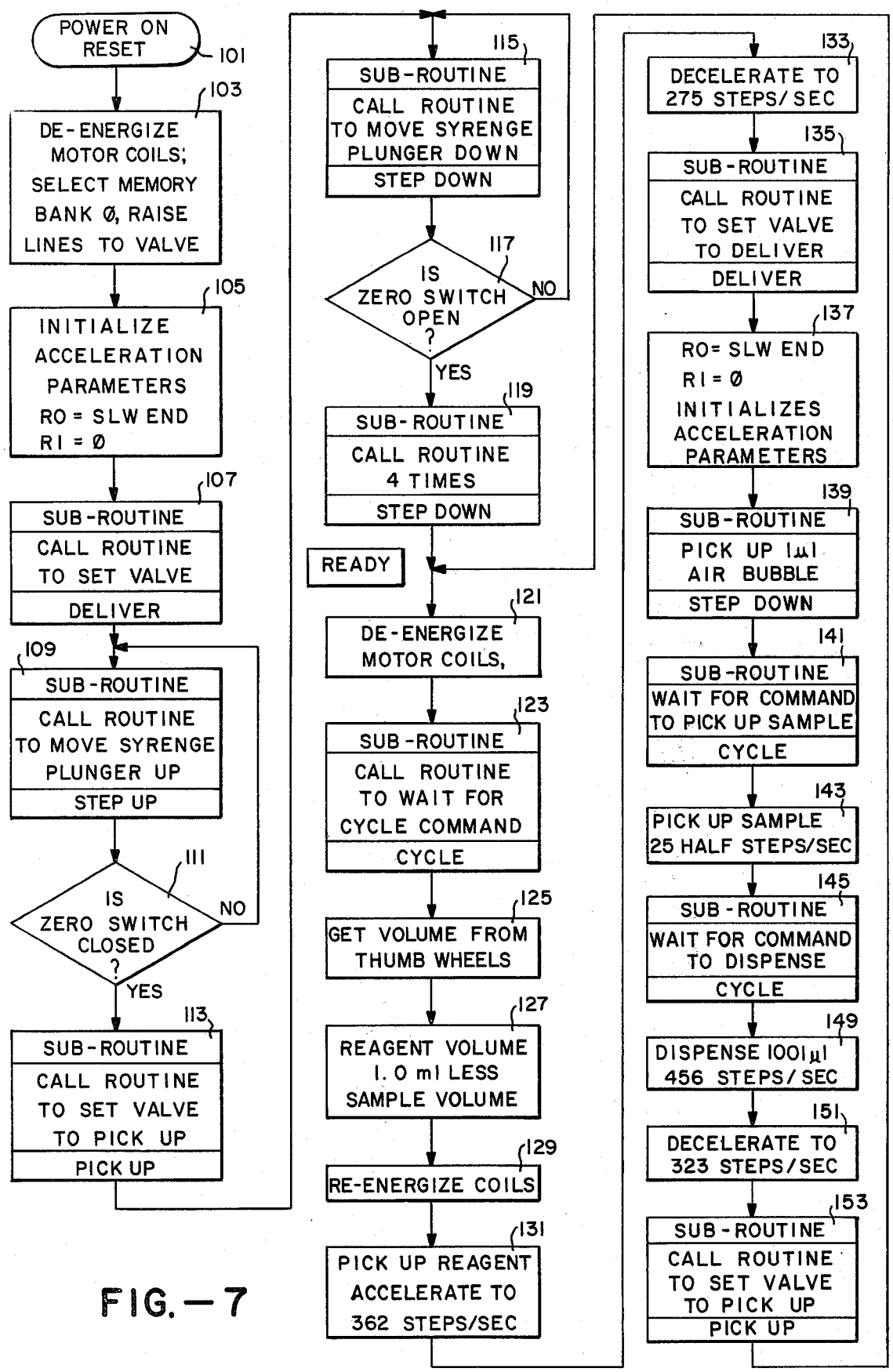
FIG.—7

METHOD FOR DILUTING A LIQUID TEST SAMPLE AND COMPUTER CONTROLLD DILUTING APPARATUS

BACKGROUND OF THE INVENTION

The present invvention relates to laboratory test equipment for analyzing liquid samples, such as blood specimens, and more particularly to automated equipment for quickly diluting liquid samples in accurate proportions with a volume of diluent which typically is substantially greater than the sample volume.

In many laboratory procedures, it is necessary to repeatedly dilute very small volumes of sample material. Normally the sample material, such as blood serum, is picked up in a relatively small volume sample syringe while the diluent is picked up by a separate diluent syringe having a relatively large volume. For example, a diluent syringe of 1000 microliters might be used with a 25 microliter sample syringe.

To increase the speed and ease of sample preparation, diluting systems have been developed which automatically operate these separate diluent and sample syringes. Such known systems automatically zero each of the two separate syringes, withdraw the syringe plungers from the syringe barrels, and reverse the movement of the syringe plungers to deliver the diluted sample. These operations can be under the push button control of an operator or under computer control. The operator or computer controlled sampling system would hold a sample probe to pick up undiluted sample from a sample receptacle and then transfer the probe to a second receptacle to deliver through the probe both the measured volume of sample and the measured volume of diluent.

One of the important design goals of such automated diluting systems is to deliver diluted samples with accuracy and reproducibility from sample to sample. However, a problem with conventional automated systems is the very fact that they require two syringes, each of which must be actuated by the system control and each of which must automatically be set to a "zero volume" before diluent and sample pick up. The present invention is a method and apparatus for the automated diluting of liquid samples with a single relatively large volume diluent syringe, that is to say, without the use of a second sample syringe. The invention permits diluting operations to occur at rapid sampling rates with high accuracy and reproducibility.

SUMMARY OF THE INVENTION

The present invention is a method for the pick up and delivery of a liquid test sample and diluent therefore by a single syringe having a barrel and a plunger wherein the syringe barrel is placed in the fluid connection with either a diluent pick-up line or a sample pick-up line by means of a fluid valving means. The method is comprised of the steps of priming the pick-up and delivery system with diluent, adjusting the syringe plunger to a zero volume setting, and with the valving means in fluid connection with the diluent pick-up line, retracting the plunger to fill the syringe barrel to a predetermined diluent volume. The valving means is then placed in fluid communication with the sample pick-up line, and thereafter the syringe plunger is further retracted to additionally fill the syringe barrel with a preset sample volume. At the end of this step, a preset volume of liquid sample has been picked up and held in the free end of the sample pick-up line. With the valving means in fluid connection with the sample pick-up line, the syringe plunger is then depressed to its zero volume setting to dispense the preset volume of liquid sample and the preset volume of diluent into a suitable receptacle.

A computer control diluting apparatus is provided for the automated pick up and delivery of a liquid test sample in accordance with the above-described method. The apparatus consists of a housing and a computer control syringe plunger drive means which includes a zero position switch means. Mounted to the housing is a computer controlled valving means which has a first branch port connectable to the diluent pick-up line and a second branch port connectable to the sample pick-up line. The valving means has a valve distribution port to which the syringe barrel is connected, and which can be switched into fluid communication with either the first or second branch ports of the switching means. Computer control means, preferably in the form of a pre-program microcomputer, is provided for sequencing the plunger drive means and the syringe valving means to first pick up diluent through the diluent pick-up line in order to fill a preset volume of the syringe barrel; secondly, to pick up sample in the sample pick-up line to fill an additional volume of the syringe barrel; and finally to deliver the sample and diluent through the sample pick-up line into a suitable receptacle for the diluted sample.

It is therefore an object of the present invention to provide a method and apparatus for the automated pick-up and delivery of a liquid test sample and diluent therefore using a single syringe which delivers diluted samples with accuracy and reproducibility. Other objects of the invention will be apparent from the following specification and claims.

DESCRIPTION OF THE DRAWINGS

FIG. 1 is a front elevation view of the apparatus of the present invention showing a syringe mounted to the distribution port of the syringe valve of the present invention.

FIG. 2 is a side elevational view showing the general assembly of the diluting apparatus of FIG. 1.

FIG. 3 provides six schematic views of a diluting apparatus illustrating the method of the invention.

FIG. 4 is a perspective view showing the zero volume switch mounted to the plunger carrier of the invention.

FIG. 5 is a partial front elevational view of the zero volume switch and plunger carrier shown in FIG. 4.

FIG. 6 is an expanded view of the tip of a sample pick-up line showing the creation of an air bubble at the tip of the line.

FIG. 7 is a flow chart illustrating the program control for the computer control means of the invention.

DETAILED DESCRIPTION OF THE PREFERRED EMBODIMENT

As above stated, one of the primary objects of the present invention is to provide for a delivery system which uses a single relatively large diameter syringe, and which does so with accuracy and reproducibility. It is noted here that the "accuracy" of the delivered volume of diluted sample will depend largely on the tolerances of the syringe used, the backlash in the delivery system, and the accuracy by which the delivery system can preset the syringe to a "zero volume" setting when the plunger is pushed in. Reproducibility, also referred to as the precision of the system, is the ability of the delivery system to repeatedly deliver a given volume within an accuracy tolerance range. This is sometimes expressed as a "cv" number where "cv" stands for the coefficient of variation in respect to the volume of many test samples. Reproducibility should not be affected by the tolerances of the syringe used.

Referring now to the drawings, the diluting apparatus, generally denoted as 11, has a housing 13 which, as shown, is generally U-shaped to provide a front plate 15, bottom plate 17 and back plate 19. A valving means, preferably in the form of a two-way syringe valve 21 having first and second branch ports 23, 25 adapted to be connected to, respectively, a diluent pick-up line 27 and a sample pick-up line 29, is secured by any suitable attachment means to the front plate 15 of the housing. A syringe 31 having barrel 33 and a plunger 35 is secured to the diluting apparatus 11 by attaching the barrel tip 34 of the syringe to the distribution port 26 of the syringe valve. With the syringe thusly secured, it can be seen that the reservoir of the syringe barrel can be switched into fluid communication with either the diluent pick-up line 27 or the sample pick-up line 29. Commercially available valves can be employed for this purpose, such as a Hamilton 3-port valve which has a 90 degree valve plug for right-angle flow and which is designed to receive standard threaded valve connectors 27(a), 29(a).

In the illustrated embodiment, the syringe plunger drive means for moving the syringe plunger up and down consists of a plunger carrier 37 slidably mounted on a guide shaft 39 which is held in axial alignment with the syringe plunger by upper and lower bearing plates 41, 43. A carrier extension 45 projects through the front panel 15 of housing 13 to releasably secure the plunger end 47 which is tapped such that it can be secured by thumb screw 48.

The plunger carrier 37 is preferably driven by a stepping motor 49 with the rotation to translation coupling between the stepping motor and the carrier being provided by a precision threaded shaft 51 rotated by a drive belt 53. The drive nut 55 on the threaded shaft 51 is held in fixed relation to the plunger carrier by a bracket means comprised of a nut guide 57 secured to plunger carrier 37, and an L-shaped leaf spring 59 secured to one end of the nut guide. The leaf spring 59 is preloaded to sandwich the drive nut 55 between the leaf spring and the nut guide to prevent the drive nut from rotating on the threaded shaft. A microswitch 61, which serves as a zero volume switch as hereinafter described and which has an output 62 which is an input to the computer control, is secured to the plunger carrier adjacent the drive nut 55.

Referring to the drive mechanism for the syringe valve 21, it is seen that the valve stem in the valve stem retainer 65 is turned by valve motor 67 through a set of spur gears 73, 75 which rotate a shaft 69 coupled to the valve stem by a valve drive collar 71. Suitable projections, such as projection 66, can be placed on the side of the spur gear 73 to mechanically trigger the lever 70 of switch 68 as the spur gear rotates. Switch 68 will provide a status input to the computer control as to the position of the syringe valve. Both the valve motor and the stepping motor are actuated by electrical input signals supplied under the control of a computer program hereinafter described. The hereinafter described program steps can be implemented by persons skilled in the art by using commercially available microelectronic parts which can be assembled to form a microcomputer (not shown) suitably located to form an integral part of the apparatus.

The operation of the apparatus shown in FIGS. 1 and 2, and the method of the present invention can best be illustrated by reference to FIG. 3 of the drawings, which shows the relative position of the syringe plunger 35 in the syringe plunger barrel 33 and the position of valve 21 in relation to the diluent pick-up line 27 and the sample pick-up line 29. Initialization of the system including zero volume set occurs with a power on or reset signal and will later be described in reference to the flow chart in FIG. 4.

When the apparatus is initialized the plunger 35 and valve 21 are in the positions shown in FIG. 3(A). When a cycle command is given by a suitable operator control command switch (not shown), diluent is picked up from the diluent receptacle through pick-up line 27 by retracting the syringe plunger from its zero volume position to a pre-established volume (D) which can be externally adjusted by the operator by, for example, thumb wheel switches (not shown). This first step is shown in FIG. 3(B) of the drawings. The diluent volume (D) will normally be large relative to the sample volume and preferably is established as a percentage of the total rated volume of the syringe used. For example, using a one thousand microliter syringe a diluent volume setting of 0.995 would be dialed on a thumb wheel graduated between zero and 1.0 to pick up 995 microliters of diluent. After the diluent is picked up, the program sequence switches the syringe valve 21 to its delivery position shown in FIG. 3(C). In this position, the syringe barrel 33 is in fluid communication with the sample pick-up line 29.

With the syringe plunger in the position shown in FIG. 3(C), a small bubble 77 of diluent will typically appear at the tip 79 of the sample pick-up line 29. (This line is primed with diluent as described below.) The larger the diameter of the sample pick-up line, the larger this diluent bubble. This diluent bubble is undesirable for the reason that it can contaminate the sample being used, and can affect the ultimate sample volume picked up and delivered. To avoid these undesirable effects, the method of the present invention preferably includes the step illustrated in FIG. 3(D), namely, the step of advancing the plunger downwardly a very slight amount to create a very small air bubble 81 at the end of the sample pick-up line (see FIG. 4). The volume of diluent now picked up by the plunger is represented in FIGS. 3(D) and 3(E) as D+. This air bubble can be achieved by picking up an additional volume of approximately one microliter.

The next step illustrated by FIG. 3(E) is to pick up the predetermined volume of sample (represented by D+S) by advancing the plunger to a specified volume of the syringe. The specified syringe volume may be the full rated volume of the syringe or a volume less than the full syringe volume, and is set by the operator. It is important to note that all operations involving pick-up of diluent, the creation of the air bubble, and the pick-up of the liquid sample involve a single direction stroke of the plunger. That is, for all these operations, the plunger is successively retracted in a downward movement to the specified volume of the syringe. This single direction stroke of the plunger for diluent and sample pick-up substantially reduces errors which might be introduced by backlash in the driving system. Significantly, there is no requirement for establishing a zero volume reference before picking up the sample as would be the case with a conventional two syringe operation.

The final step of the sample and diluent pick-up and delivery method of the present invention is illustrated in FIG. 3(F) and consists of depressing the plunger to the full extent of the syringe barrel to deliver a volume of sample and diluent equal to the specified volume of the syringe. The volume is delivered by slewing the plunger stroke rate to obtain good vortexing of the fluid in the receptacles used for receiving the diluted sample volume. The smaller the diameter of the delivery tube, the greater the fluid velocity will be and hence the greater the mixing. Again, it is noted that not only are small diameter sample lines desirable for improved mixing action, but also, for increased accuracy and precision of sampling, to reduce the diluent bubble which normally forms at the end of the line.

In respect to the above discussion it is understood that the sample pick-up line may be terminated by a hand-held sample probe which is held by the operator.

It is noted that the apparatus, including the syringe barrel 33, syringe valve 21, and sample pick-up line 29, is fully primed by simply cycling the syringe and syringe valve several times without picking up a liquid sample. This avoids air spaces in the delivery system, such as occurs when liquid is picked up by a conventional syringe through a syringe needle. The air volume picked up by a conventional syringe would be equal to the volume of the air in the needle between the needle's end and the plunger tip. The elimination of this air space is important since air is compressible and will affect volume accuracy and precision with respect to the delivered samples. It is also noted that the accuracy and precision of the results, especially when using very small sample pick-up lines and small diameter sample syringes, might be affected by adhesion of liquid to the walls of the sample pick-up lines where an air pocket exists. A fully primed system such as provided by the present invention eliminates this possible source of error.

Referring now to FIG. 6, there is shown a flow chart for the program control of the apparatus of the present invention. From this flow chart, it is seen that the system is initialized upon activating the power on switch (not shown) or a reset switch (not shown) as indicated by block 101 at the top of the flow chart. The program sequence provides initially for de-energizing the motor coils of the valve motor 67 by an I/O instruction which sets the appropriate output lines of the selected microprocessor to the inactive state, and for initializing acceleration parameters for the stepping motor 49 (blocks 103, 105). The program sequence continues by calling a "delivery" subroutine 107 which sets the syringe valve 21 to its delivery position, that is, to a position which places it in fluid communication with the sample pick-up tube 29. A subsequent subroutine denoted 109 then moves the syringe plunger 35 up until a logic branch (block 111) detects whether or not the microswitch 71 is closed. When closing of the micro-switch is sensed, additional subroutines switch the syringe valve 21 to the sample pick-up position and move the syringe plunger down until the zero position micro-switch is opened (blocks 113, 115, 117). When the program detects the opening of the microswitch 61, a further subroutine can be provided (block 119) to move the syringe plunger further downward in order to compensate for the compression of the plunger tip. With the syringe plunger thusly placed in a zero volume position, the zero location is stored in memory and the power on or reset initialization is complete and the program is "ready."

When ready, the program de-energizes the motor coils of the stepping and valve motors 49, 67, and waits for a command (blocks 121, 123). When a run command is given by an operator, the program gets the sample volume from the volume setting of the apparatus (not shown) and determines the diluent volume by subtracting the specified volume of the syringe set by the operator, for example, 1,000 microliters, from the sample volume also set by the operator (blocks 125, 127). Under program control, the motor coils are then reenergized and the plunger moved at a chosen slew rate to pick up the indicated diluent volume (blocks 129, 131, 133). The program then calls a subroutine to set the valve to its deliver position, that is, into fluid communication with the sample pick-up tube 29 (block 135), and, after initializing acceleration parameters as indicated by block 137, the stepping motor is stepped to move the syringe plunger 35 a further but slight distance downward in order to pick up an approximately one microliter air bubble (block 139). The program then waits for a command to pick up a sample which the operator gives after he or she places the probe tip of the sample pick-up line into the sample reservoir (block 141). The sample is preferably picked up by advancing the stepping motor in half steps at a relatively slow rate, for example, of 25 half steps per second (block 143). Software for advancing a stepping motor in half steps is readily available in the trade and can be generally obtained from a stepping motor manufacturer. A stepping motor manufactured by North American Phillips with available half-step program routines can be used.

Once the sample has been picked up in the end of the sample probe, the program control waits for a dispense command from the operator which is given once the operator places the sample pick-up probe into a suitable receptacle for receiving the diluted sample (block 145). Upon receiving a command, the premeasured volume of sample and diluent is dispensed by moving the plunger in reference to the zero volume position which is stored in the memory of the microcomputer. The slew rate of the plunger and hence the rate at which the fluid is dispensed is controlled by the program as denoted by blocks 149, 151. When the fluid has been dispensed, a subroutine is called for setting the syringe valve back to the diluent pick-up position (block 153), whereupon the program is returned to its ready state to wait for a command cycle after de-energizing the motor coils (blocks 121, 123).

The program which has heretofore been described can be implemented on an Intel 8035 microprocessor.

Therefore, it can be seen that the present invention is an improved method for diluting a liquid test sample with a diluent and a computer controlled diluting apparatus for implementing the method of the invention. The apparatus and method provide significant and unexpected improvement in automated sampling devices, in that, they permit diluting to be achieved with accuracy and precision with a single diluent syringe, substantially reducing the cumulative errors which occur with the operation of the separate sample and diluent syringes.

Although the present invention has been described above in considerable detail, it is not intended that the invention be limited to such detail, except as may be necessitated by the appended claims.

What we claim is:

1. A computer controlled diluting apparatus for the automated pick-up and delivery of a liquid test sample and diluent therefor by a syringe having a barrel, barrel tip, and plunger, said apparatus comprising
   a housing,
   a computer controlled syringe plunger drive means including a zero volume switch means,
   computer controlled valve means mounted to said housing, said valve means having a first branch port adapted to be connected to a diluent pick-up line, a second branch port adapted to be connected to a sample pick-up line, and a distribution port which can be switched into fluid communication with either said first or second branch ports, said distribution port being adapted to releasably secure the barrel tip of a syringe, and
   computer control means for sequencing said plunger drive means and said syringe barrel valve means to:
   (a) pick up diluent through said diluent pick-up line to fill a preset volume of said syringe barrel,
   (b) pick up sample in said sample pick-up line to fill and additional volume of said syringe barrel, and
   (c) deliver sample and diluent through said sample pick-up line.

2. The apparatus of claim 1 wherein said plunger drive means includes
   a guide shaft,
   a plunger carrier slidably mounted on said guide shaft and adapted to releasably engage the free end of a plunger of a syringe which has its barrel tip secured to the distribution port of said valve means,
   a stepping motor, and
   rotation to translation coupling between said stepping motor and said plunger carrier to permit said stepping motor to drive the plunger carrier on said guide shaft.

3. The apparatus of claim 2 wherein said rotation to translation coupling between said stepping motor and plunger carrier includes a rotatable precision threaded shaft rotatably coupled to said stepping motor, a drive nut threaded on said shaft, and bracket means for holding said drive nut in fixed relation to said plunger carrier.

4. The apparatus of claim 3 wherein said zero volume switch means includes a leaf spring forming part of the bracket means holding said drive nut in fixed relation to said plunger carrier, and a switch secured to said bracket means, said leaf spring being preloaded to actuate said switch until a force resisting the forward motion of said plunger is encountered when the plunger tip reaches the end of the plunger barrel whereupon the resisting force overcomes the preloaded force of said leaf spring thereby releasing same from said switch, said switch having an output capable of being detected by said computer control means.

5. A method for the pick-up and delivery of a liquid test sample and diluent therefor by a single syringe having a barrel and plunger wherein said syringe barrel is placed in fluid connection with either a diluent pick-up line or a sample pick-up line by means of a syringe valve means, said method comprising the steps of
   priming the syringe barrel, syringe valve means, diluent pick-up line and sample pick-up line with diluent,
   adjusting the syringe plunger to a zero volume setting,
   with the valving means in fluid connection with said diluent pick-up line, retracting said plunger to fill said syringe barrel to a predetermined diluent volume,
   placing said valve means in fluid communication with said sample pick-up line,
   further retracting said syringe plunger to additionally fill said syringe barrel with a preset sample volume whereby a preset volume of liquid sample is picked up and held in the free end of said sample pick-up line, and
   with the syringe valve means in fluid connection with said diluent pick-up line, depressing said plunger to its zero volume setting to thereby dispense said preset volume of liquid sample and diluent into a suitable receptacle.

6. The method of claim 5 further including the step of slightly retracting said syringe plunger after the step of placing said syringe valve means in fluid connection with said sample pick-up line but before retracting the plunger to pick up a liquid sample, said slight retraction being of a degree which causes an air bubble to form in the free end of said sample pick-up line.

7. The method of claim 5 wherein retracting and depressing said syringe plunger is achieved by plunger drive means having a stepping motor as a drive source.

8. The method of claim 7 wherein said stepping motor is advanced in whole steps at a predetermined rate when diluent is picked up and the sample and diluent are delivered, and in half steps at a predetermined rate when the liquid sample is picked up.

9. The method of claim 5 wherein the total rated volume of the syringe barrel is filled after the step of picking up the liquid sample and the volume of diluent picked up through said diluent pick-up line is determined by a percentage of the barrel volume.

* * * * *